United States Patent
Fujishima et al.

[19]

[11] Patent Number: 5,855,595
[45] Date of Patent: *Jan. 5, 1999

[54] TUMOR TREATMENT APPARATUS

[75] Inventors: Akira Fujishima, 710-5 Nakamaruko, Nakahara-ku, Kawasaki-shi, Kanagawa-ken; Kazuhito Hashimoto, 2000-10, Kosugaya-cho, Sakae-ku, Yokohama-shi, Kanagawa-ken; Yoshinobu Kubota, 1697-28, Mutsuura-cho, Kanazawa-ku, Yokohama-shi, Kanagawa-ken; Rensuke Adachi; Teruyuki Kakeda, both of Tokyo, all of Japan

[73] Assignees: Asahi Kogaku Kogyo Kabushiki Kaisha, Tokyo; Akira Fujishima, Kanagawa-ken; Kazuhito Hashimoto, Kanagawa-ken; Yoshinobu Kubota, Kanagawa-ken, all of Japan

[*] Notice: This patent issued on a continued prosecution application filed under 37 CFR 1.53(d), and is subject to the twenty year patent term provisions of 35 U.S.C. 154(a)(2).

[21] Appl. No.: 416,321

[22] Filed: Apr. 4, 1995

[30] Foreign Application Priority Data

Apr. 4, 1994 [JP] Japan ................................. 6-066136

[51] Int. Cl.⁶ ................................................. A61N 5/00
[52] U.S. Cl. ............................. 607/90; 606/3; 250/504 R
[58] Field of Search .................................. 607/88–90, 94; 606/23; 128/633; 250/504 R, 495.1, 493.1

[56] References Cited

U.S. PATENT DOCUMENTS

| | | |
|---|---|---|
| 4,053,756 | 10/1977 | Takashashi . |
| 4,298,005 | 11/1981 | Mutzhas ................................. 607/54 |
| 4,444,190 | 4/1984 | Mutzhas . |
| 4,686,986 | 8/1987 | Fenyo et al. ............................. 607/90 |
| 5,344,433 | 9/1994 | Talmore ................................... 607/88 |
| 5,344,434 | 9/1994 | Talmore . |
| 5,405,368 | 4/1995 | Eckhouse ................................. 607/90 |
| 5,441,531 | 8/1995 | Zarate et al. ............................ 607/90 |

FOREIGN PATENT DOCUMENTS

| | | |
|---|---|---|
| 2342745 | 9/1977 | France . |
| 9012470 | 1/1991 | Germany . |
| 4244429 | 7/1993 | Germany . |
| 62087526 | 4/1987 | Japan . |
| 5-60449 | 2/1993 | Japan . |
| 7702254 | 9/1977 | Netherlands . |
| 2105195 | 3/1993 | United Kingdom . |
| 2272278 | 5/1994 | United Kingdom . |
| 85/00527 | 2/1985 | WIPO . |
| 9909850 | 5/1994 | WIPO ..................................... 607/88 |

OTHER PUBLICATIONS

WPI Abstract Accession No. 87–0152456/22.
United Kingdom Search Report.
Cai, R. et al, "Induction of Cytotoxicity by Photoexited Tio2 Particles," Cancer Research 52, pp. 2346–2348, Apr. 15, 1992.
Copy of a French Search Report, dated Jun. 5, 1998.

*Primary Examiner*—Robert L. Nasser
*Attorney, Agent, or Firm*—Greenblum & Bernstein, P.L.C.

[57] ABSTRACT

A tumor treatment apparatus is provided including a light source which emits a bundle of light including ultraviolet radiation, visible radiation and infrared radiation. Also provided are an infrared radiation filter which filters infrared radiation, a visible radiation filter which filters visible radiation, and an optical fiber which transmits a bundle of light transmitted through the infrared radiation filter and the visible radiation filter toward an affected part of a patient to be treated.

29 Claims, 6 Drawing Sheets

TUMOR TREATMENT APPARATUS

BACKGROUND OF THE INVENTION

1. Field of the Invention

The present invention relates to a tumor treatment apparatus in which light of a continuous spectrum including an ultraviolet spectrum, a visible spectrum, and an infrared spectrum, emitted from a light emitting lamp is radiated through an optical fiber through which ultraviolet light can be transmitted, onto an area of tissue of a living body in which $TiO_2$ has been administered.

2. Description of Related Art

The inventors of the present invention have found that when $TiO_2$ (titanium dioxide) is administered in a living body, a higher density of $TiO_2$ is absorbed by tumorigenic cell than by a normal cell. If the tumorigenic cell receives an electromagnetic wave having a wavelength ranging from X-ray to ultraviolet, $TiO_2$ is excited, so that the tumorigenic cell can be destroyed due to an active oxygen which is produced during the excitation. An antineoplastic agent containing $TiO_2$ excited by the electromagnetic wave, as mentioned above has been proposed by the assignee of the present application (Japanese Examined Patent Publication No. 5-60449).

As mentioned above, $TiO_2$ is excited by an electromagnetic wave having a wide band wavelength of less than around 400 nm. In general, a commercially available ultraviolet emitting apparatus, such as a 500 W extra-high pressure mercury-vapor lamp is used to radiate an entire range of ultraviolet light of around 300 to 400 nm onto an affected area.

To radiate ultraviolet light onto a specific affected area within a body cavity, it is advisable to use an endoscope having a forceps channel in which a quartz fiber, or the like, through which ultraviolet light can be transmitted is inserted, so that the radiation of ultraviolet light can be carried out while observing the affected area through the quartz fiber.

However, the light source (lamp) for the ultraviolet light emitting apparatus emits not only ultraviolet light but also visible light. Consequently, visible light energy is absorbed by an area of tissue of a living body; although, the absorption rate of visible light is smaller than that of ultraviolet light. This causes the temperature of the normal cell of the biotic tissue to increase.

SUMMARY OF THE INVENTION

The primary object of the present invention is to provide a tumor treatment apparatus in which only ultraviolet light of a wavelength of around 300 nm to 400 nm can be safely radiated onto an area of biotic tissue in which $TiO_2$ has been administered without fearing destruction of normal cells due to the radiation of visible light.

To achieve the object mentioned above, according to the present invention, there is provided a tumor treatment apparatus comprising a light source which emits a bundle of light including ultraviolet radiation, visible radiation and infrared radiation; an infrared radiation filter which filters (cuts) infrared radiation; a visible radiation filter which filters (cuts) visible radiation; and a light transmitting mechanism for transmitting a bundle of light transmitted through the infrared radiation filter and the visible radiation filter to radiate the same onto an affected area to be treated.

Preferably, the light transmitting mechanism is formed by a quartz fiber.

The infrared radiation filter can be comprised of a reflecting mirror which reflects the light emitted from the light source toward an incident end of the light transmitting mechanism.

The visible radiation filter is preferably provided between the reflecting mirror and the light transmitting mechanism.

In an embodiment, the infrared radiation filter filters light whose wavelength is greater than 700 nm, and the visible radiation filter filters light whose wavelength is around 400 nm to 700 nm.

Preferably, the visible radiation filter filters light whose wavelength is around 400 nm to 700 nm by approximately 70 to 90%.

The visible radiation filter can be selectively and retractably moved in an optical path. The light source emits light of a continuous spectrum including an ultraviolet spectrum, a visible spectrum and an infrared spectrum.

The light source can be made of a xenon lamp.

According to another aspect of the present invention, there is provided a tumor treatment apparatus which emits light of a continuous spectrum including an ultraviolet spectrum, a visible spectrum and an infrared spectrum, emitted from a light source lamp, onto an area of tissue of a living body in which $TiO_2$ has been administered through an optical fiber through which ultraviolet light can be transmitted, including an infrared radiation filter which filters infrared light of the light emitted from the light source lamp before the light is made incident upon the optical fiber, and a visible radiation filter which filters visible light whose wavelength is around 400 to 700 nm, emitted from the light source lamp before the light is made incident upon the optical fiber.

In an embodiment, the visible radiation filter partially filters visible light whose wavelength is around 400 to 700 nm, so that the mean intensity of the visible light to be made incident upon the optical fiber is smaller than that of the ultraviolet light whose wavelength is around 300 to 400 nm. It is possible for the visible radiation filter to cut visible light of around 400 to 700 nm at an average filtration rate of approximately 70 to 90%. With this arrangement, ultraviolet light can be radiated on an affected area to be treated, while illuminating the affected area with the visible light, which enables an operator to observe the affected area. The visible radiation filter can be retractably inserted in an optical path between the light source lamp and an incident end of the optical fiber.

The present disclosure relates to subject matter contained in Japanese Patent Application No. 06-66136 (filed on Apr. 4, 1994) which is expressly incorporated herein by reference in its entirety.

BRIEF DESCRIPTION OF THE DRAWINGS

The invention will be described below in detail with reference to the accompanying drawings, in which.

DESCRIPTION OF THE PREFERRED EMBODIMENT

Figure 1:
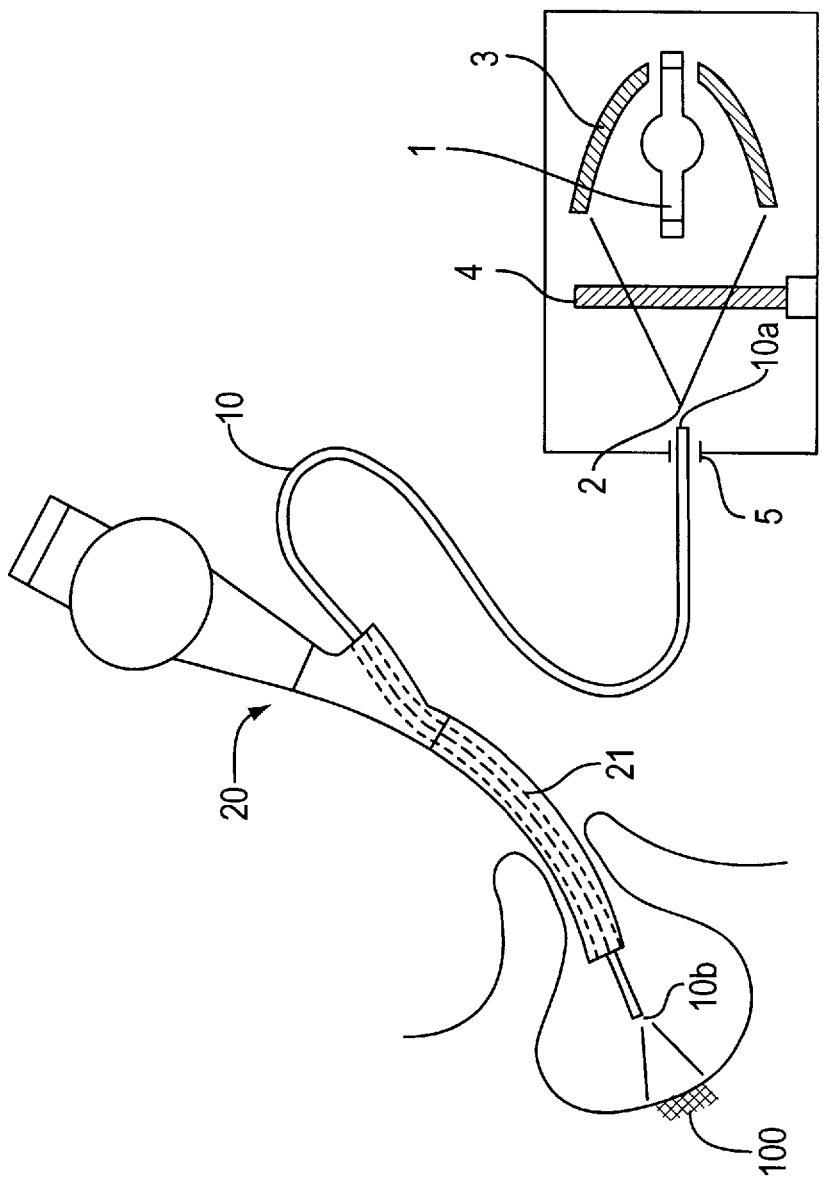
FIG. 1 is a schematic view of an entire structure of a tumor treatment apparatus according to a first embodiment of the present invention.
Figure 2:
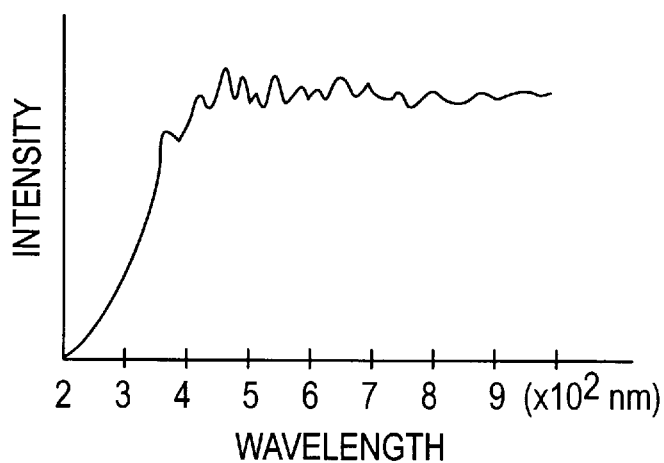
FIG. 2 is a diagram of characteristics of a light source lamp in the first embodiment shown in FIG. 1.

FIG. 1 shows an entire structure of a first embodiment of the present invention. In FIG. 1, a light source 1 is in the form of a xenon lamp which emits light (i.e. a light beam, a bundle of light, or light rays) of a continuous spectrum including an ultraviolet range, a visible range and an infrared range, as shown in FIG. 2. However, the light source is not limited a xenon lamp, as long as the light source emits light of a continuous spectrum.

Figure 3:
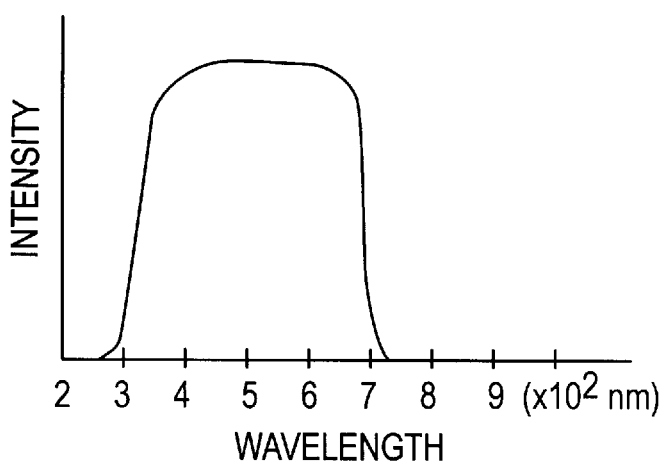
FIG. 3 is a diagram of characteristics of an infrared radiation filter in the first embodiment shown in FIG. 1.

The light source 1 is provided with a reflecting mirror 3 which converges the light emitted from the light source 1 to a convergent point 2. The characteristics of the reflected light are such that infrared radiation whose wavelength is greater than around 700 nm cannot be reflected, as shown in FIG. 3. Hence, the reflecting mirror 3 constitutes an infrared filter which filters infrared radiation. Consequently, there is little or no infrared light in a bundle of light to be converged onto the convergent point 2.

Figure 4:
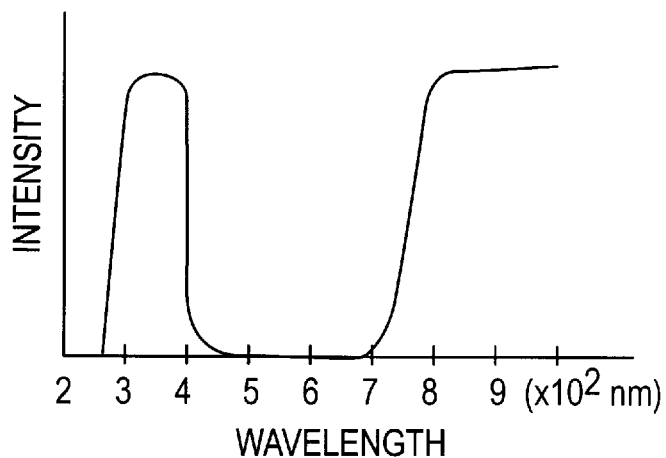
FIG. 4 is a diagram of characteristics of a visible radiation filter in the first embodiment shown in FIG. 1.

A visible radiation filter 4 is provided in an optical path between the reflecting mirror 3 and the convergent point 2 and substantially intercepts and filters visible light whose wavelength is around 400 nm to 700 nm, as shown in FIG. 4. Consequently, light transmitted through the visible radiation filter 4 to be converged onto the convergent point 2 contains only ultraviolet light whose wavelength is around 300 nm to 400 nm.

An incident end 10a of an optical fiber 10 is located at or in the vicinity of the convergent point 2. The optical fiber (quartz fiber) 10 has a core made of quartz through which ultraviolet radiation of at least 300 nm to 400 nm can be transmitted. The optical fiber 10 can be inserted in and removed from a supporting connector 5 of the treatment apparatus, so that the incident end (light receiving end) 10a of the optical fiber 10 is located at or in the vicinity of the convergent point 2.

The quartz fiber 10 is inserted in a forceps channel 21 of an endoscope 20. The endoscope is provided therein with an optical viewing system and an optical illuminating system (not shown) etc. Any type of endoscope having a forceps channel in which a quartz fiber can be inserted can be used.

As can be seen in FIG. 1, ultraviolet light having a wavelength of around 300 nm to 400 nm can be emitted from an emission end 10b of the quartz fiber 10 toward an affected part 100 to be treated within a body cavity.

Therefore, if $TiO_2$ is administered in advance to the affected area 100, when the latter receives ultraviolet radiation, the tumorous cell can be destroyed. Since a light component other than ultraviolet radiation is not emitted from the quartz fiber 10, that is, since neither visible radiation nor infrared radiation are emitted from the quartz fiber, little or no increase in the temperature of the affected area 100 occurs.

Figure 5:
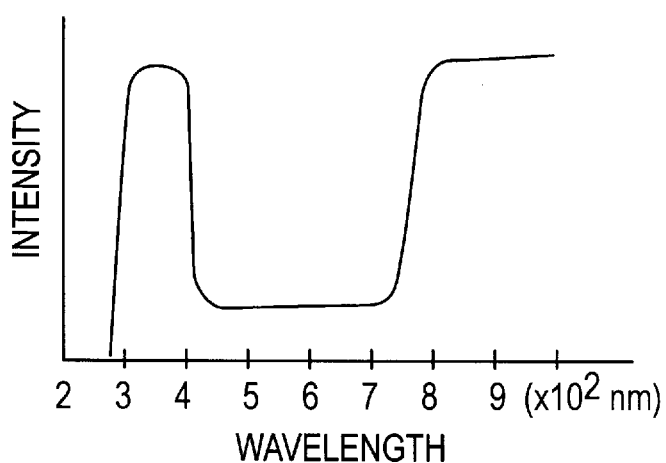
FIG. 5 is a diagram of characteristics of a visible radiation filter according to a second embodiment of the present invention.

FIG. 5 shows the optical characteristics of a visible radiation filter 4 according to a second embodiment of the present invention. The visible radiation filter 4 does not completely filter all visible light whose wavelength is about 400 nm to 700 nm, but instead partially filters visible light, so that the light transmitted through the visible light filter 4 has a mean intensity of about 300 to 400 nm which is lower than that of ultraviolet light.

Consequently, the affected area 100 is prevented from being heated to a high temperature at which a burn is produced. Moreover, the affected area 100 can be illuminated by the visible light, so that the affected area 100 can be clearly observed. To this end, preferably, the visible light filter 4 absorbs approximately 70 to 90% (on an average) of the visible light having a wavelength of 400 nm to 700 nm.

Figure 6:
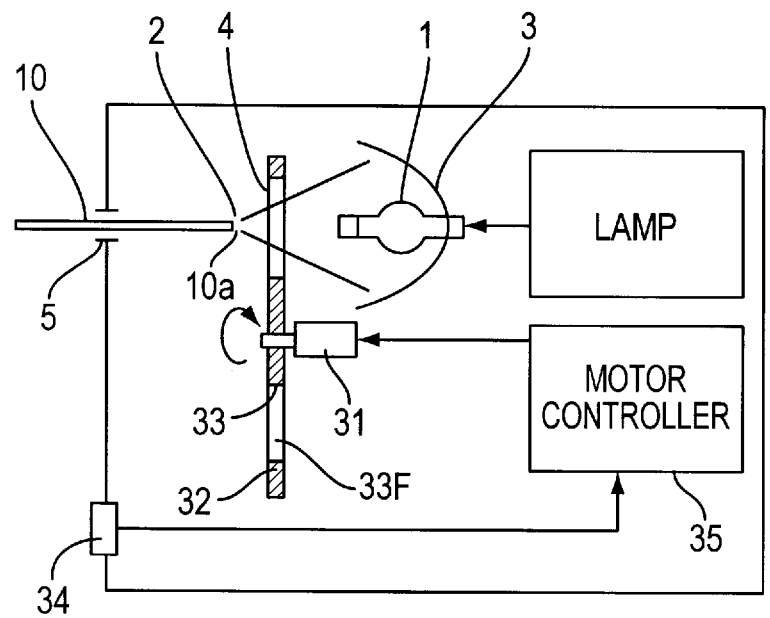
FIG. 6 is a schematic view of a tumor treatment apparatus according to a third embodiment of the present invention.
Figure 7:
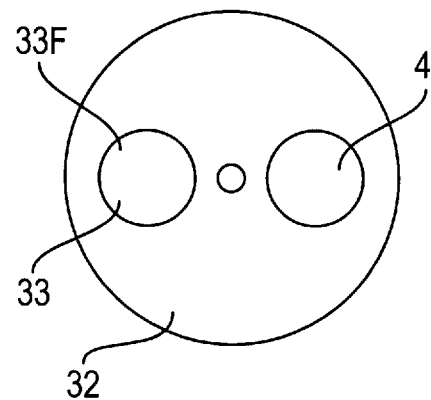
FIG. 7 is the front elevational view of a turret in a third embodiment of the present invention.

FIGS. 6 and 7 show a third embodiment of the present invention, in which the visible light filter 4 is provided in an optical path between the lamp 1 and the convergent point 2 (i.e., the incident end 10a of the quartz fiber 10).

In the third embodiment, the visible radiation filter 4 is provided on an opaque turret 32 which is rotated by a motor 31 so as to selectively occupy two stop positions. The turret 32 is also provided with a through hole 33 which is located in a symmetrical arrangement with respect to the center of the turret 32, as shown in FIG. 7. Namely, the visible light filter 4 and the through hole 33 are located along a diameter of the turret. The visible light filter 4 and the through hole 33 are selectively brought into the optical path when the turret 32 is rotated by the motor 31. The motor 31 is controlled by a motor controller 35, so that the motor 31 rotates the turret 32 to selectively come to a first stop position at which the visible light filter 4 is located in the optical path or a second stop position at which the through hole 33 is located in the optical path.

With this arrangement, when the visible light filter 4 is located in the optical path (first stop position), the mode of operation of the apparatus according to the third embodiment is the same as that of the first or second embodiments. When the through hole 33 is located in the optical path (second stop position), the system shown in FIG. 6 functions as a conventional ultraviolet light emitter which emits light including an ultraviolet light component having wavelengths around 300 to 400 nm and a visible light component having wavelengths around 400 to 700 nm toward the convergent point 2.

Figure 8:
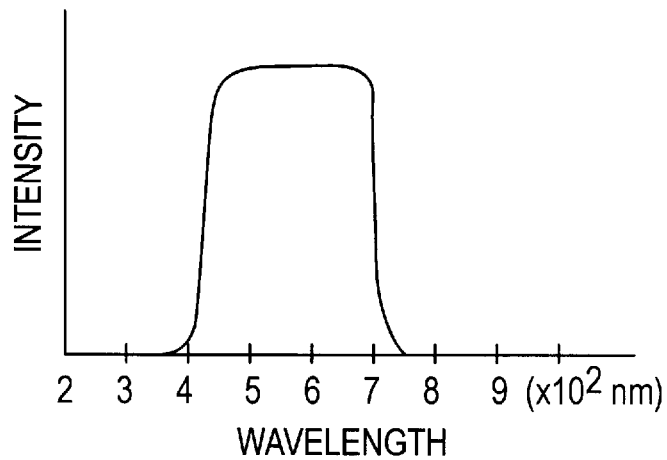
FIG. 8 is a diagram of characteristics of a filter in the third embodiment of the present invention.

If a filter 33F which permits only visible light having wavelengths around 400 nm to 700 nm to pass therethrough, as shown in FIG. 8 is attached to the through hole 33, only the visible light can reach the convergent point 2. Hence, the filter 33F makes it possible to use the optical system shown in FIG. 6 as an illuminating light source for an endoscope.

Figure 9:
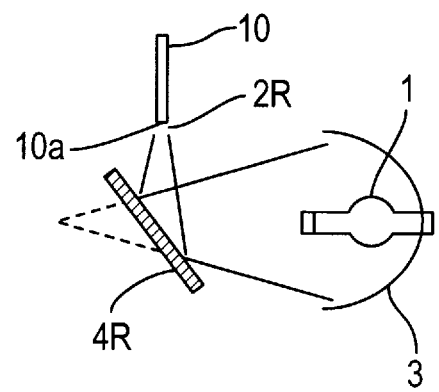
FIG. 9 is a schematic view of a tumor treatment apparatus according to a fourth embodiment of the present invention.

FIG. 9 shows a fourth embodiment of the present invention, in which the visible light filter 4 is replaced with a plane mirror 4R which is obliquely provided in the optical path at a predetermined inclination angle. The inclination angle of the plane mirror 4R is such that a bundle of light reflected thereby is converged onto a convergent point 2R at which the incident end 10a of the quartz fiber 10 is located. The characteristics of the plane mirror 4R are such that the reflected light (not transmitted light) exhibits the intensity distribution as shown in FIG. 4 or 5.

Figure 10:
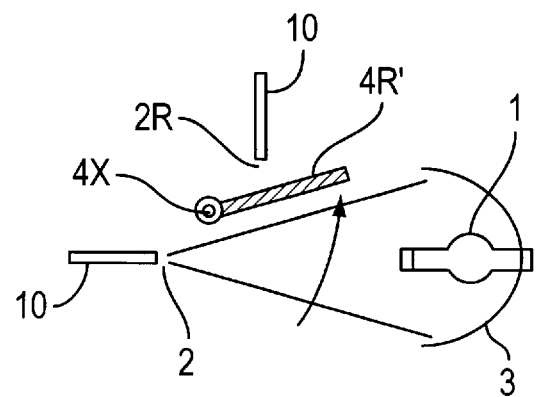
FIG. 10 is a schematic view of a tumor treatment apparatus according to a fifth embodiment of the present invention.

FIG. 10 shows a fifth embodiment of the present invention, in which the plane mirror 4R shown in FIG. 9 is replaced with a rotatable plane mirror 4R' which is rotatable about a shaft 4X, so that the rotatable plane mirror 4R' can be selectively brought into the optical path and retracted from the optical path. When the rotatable plane mirror 4R' is retracted from the optical path, both visible light and ultraviolet light can be made incident upon the quartz fiber 10, as in the third embodiment illustrated in FIG. 6. In the fifth embodiment, the quartz fiber 10 must be moved between the position "2" when the rotatable plane mirror 4R' is located in the optical path and the position "2R" when the rotatable plane mirror 4R' is retracted from the optical path, as shown in FIG. 10. Alternatively, it is possible to provide separate fibers for the two positions, respectively.

Figure 11:
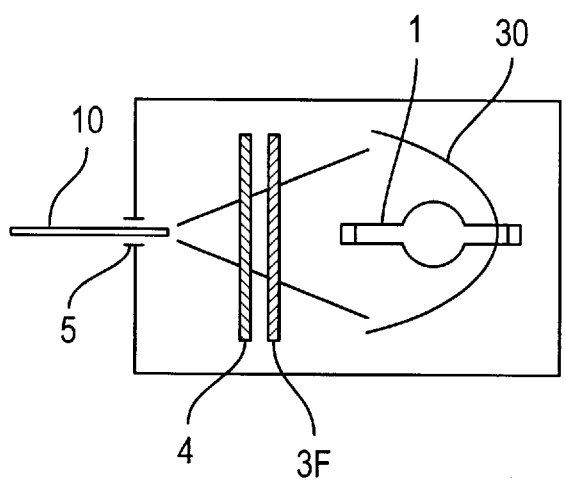
FIG. 11 is a schematic view of a tumor treatment apparatus according to a sixth embodiment of the present invention; and, FIG. 12 is a side elevational view of an emission end of an improved quartz fiber according to the present invention.

FIG. 11 shows a sixth embodiment of the present invention, in which the reflecting mirror 30 for the lamp 1 reflects light of a total wavelength range including infrared light. In connection with the characteristics of the reflecting mirror 30, the infrared light filter 3F which absorbs infrared light to filter the same is provided in the optical path, in juxtaposition with the visible light filter 4.

Note that when the xenon lamp is used as the light source 1 in the embodiments mentioned above, there is minimum light incident upon the quartz fiber 10 in the axial direction thereof. Consequently, there is a possibility that the emission range of light from the quartz fiber 10 is in the form of a doughnut (annulation).

Figure 12:
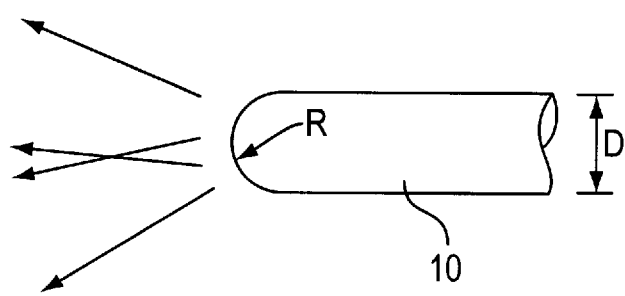

To prevent this, the emission end surface of the quartz fiber 10 is preferably convex (or concave FIG. 12), so that the light to be emitted therefrom is refracted at the emission end surface toward the center portion of the doughnut shape to thereby uniformly distribute the illuminating light. To this end, the radius R of the convex or concave end surface of the quartz fiber 10 is preferably selected such that $10D \leq R \leq D$, wherein D designates the diameter of the quartz fiber 10.

As can be understood from the above discussion, an infrared light component and a visible light component contained in light of a continuous spectrum that is emitted from a light source and that includes an ultraviolet radiation spectrum, a visible radiation spectrum and an infrared radiation spectrum are removed before reaching the optical fiber, so that only the ultraviolet radiation can be made incident upon the optical fiber. Consequently, if the light is radiated onto an affected area of a biotic tissue, there is little or no increase in the temperature of the affected area. Thus, the biotic tissue in which $TiO_2$ is administered in advance can be safely radiated by only the ultraviolet light so as to effectively destroy the tumorous cells without destroying normal cells.

We claim:

1. A tumor treatment apparatus for treating an affected area, said tumor treatment apparatus comprising:
    a light source which emits a beam of light including ultraviolet radiation, visible radiation and infrared radiation;
    an infrared radiation filter for filtering infrared radiation;
    a visible radiation filter for filtering visible radiation, said visible radiation filter filtering only a predetermined portion of the visible radiation emitted by said light source; and
    a system that transmits a beam of light including ultraviolet radiation and filtered visible radiation, transmitted through said infrared radiation filter and said visible radiation filter, to radiate said beam of light including ultraviolet radiation and filtered visible radiation onto an affected area to be treated.

2. A tumor treatment apparatus according to claim 1, wherein said light transmitting means comprises a quartz fiber.

3. The tumor treatment apparatus according to claim 2, an end surface of said quartz fiber having a radius R such that $10D \leq R \leq D$, where D represents a diameter of said quartz fiber.

4. A tumor treatment apparatus according to claim 1, wherein said infrared radiation filter is comprised of a reflecting mirror which reflects said light emitted from said light source toward an incident end of said light transmitting means.

5. A tumor treatment apparatus according to claim 4, wherein said visible radiation filter is provided between said reflecting mirror and said light transmitting means.

6. A tumor treatment apparatus according to claim 1, wherein said infrared radiation filter filters light having a wavelength greater than 700 nm.

7. A tumor treatment apparatus according to claim 1, wherein said visible radiation filter filters light having a wavelength that is around 400 nm to 700 nm.

8. A tumor treatment apparatus according to claim 1, wherein said light source emits light of a continuous spectrum including an ultraviolet spectrum, a visible spectrum and an infrared spectrum.

9. A tumor treatment apparatus according to claim 8, wherein said light source is a xenon lamp.

10. The tumor treatment apparatus according to claim 1, said light source positioned between said infrared radiation filter and said visible radiation filter.

11. The tumor treatment apparatus according to claim 1, said visible radiation filter being adapted to filter approximately 70% to 90% of light having a wavelength between about 400 nm to 700 nm.

12. The tumor treatment apparatus according to claim 1, wherein said visible radiation filter can be selectively inserted into and retracted from an optical path of the beam of light.

13. The tumor treatment apparatus according to claim 12, said visible radiation filter being mounted on a turret that is rotatable to move said visible radiation filter into and out of the optical path of the beam of light.

14. The tumor treatment apparatus according to claim 13, said turret including an aperture diametrically opposite to said visible filter, whereby filtered or unfiltered visible light can be emitted onto an affected area to be treated, in accordance with a position of said turret.

15. A tumor treatment apparatus comprising:
    a light source which emits a beam of light including ultraviolet radiation, visible radiation, and infrared radiation;
    an infrared radiation filter that filters infrared radiation;
    a visible radiation filter that filters visible radiation;
    a light transmitting system that transmits a beam of light comprising ultraviolet and visible radiation, transmitted through said infrared radiation filter and said visible radiation filter, so that said beam of light comprising ultraviolet radiation is incident onto an affected area to be treated; and
    a positioning system that selectively positions said visible radiation filter in and out of said beam of light, whereby the beam of light transmitted through said light positioning system can include ultraviolet radiation and unfiltered visible radiation or can include ultraviolet radiation and filtered visible radiation.

16. A tumor treatment apparatus which emits light of a continuous spectrum including an ultraviolet spectrum, a visible spectrum and an infrared spectrum, said light being emitted from a light source lamp, said tumor treatment apparatus adapted for emitting light of the continuous spectrum onto an area of tissue of a living body in which $TiO_2$ has been administered, said light being transmitted through an optical fiber through which ultraviolet light can be transmitted, said tumor treatment apparatus comprising:

an infrared radiation filter for filtering infrared light of said light emitted from said light source lamp before said light is made incident upon said optical fiber; and, a visible radiation filter for filtering only a predetermined portion of visible light having a wavelength that is around 400 nm to 700 nm emitted from said light source lamp before said light is made incident upon said optical fiber.

17. The tumor treatment apparatus according to claim 16, wherein the optical fiber comprises a quartz fiber.

18. The tumor treatment apparatus according to claim 16, said infrared radiation filter and said visible radiation filter being positioned on opposite sides of said light source lamp.

19. The tumor treatment apparatus according to claim 16, wherein said visible radiation filter is adapted to filter visible light having a wavelength that is around 400 to 700 nm, so that a mean intensity of the visible light incident upon said optical fiber is lower than that of ultraviolet light having a wavelength that is around 300 to 400 nm.

20. The tumor treatment apparatus according to claim 19, wherein said visible radiation filter is adapted to filter visible light having a wavelength that is around 400 to 700 nm at an average filtration rate of approximately 70% to 90%.

21. The tumor treatment apparatus according to claim 16, wherein said visible radiation filter is mounted to be inserted into and retracted from an optical path between said light source lamp and an incident end of said optical fiber.

22. The tumor treatment apparatus according to claim 21, said visible radiation filter being mounted on a turret that is rotatable to insert said visible radiation filter into and retract said visible radiation filter from said optical path.

23. The tumor treatment apparatus according to claim 22, said turret including an aperture diametrically opposite to said visible filter, whereby filtered or unfiltered visible light can be emitted onto an affected area to be treated in accordance with a position of said turret.

24. The tumor treatment apparatus according to claim 16, an end surface of said optical fiber having a radius R such that $10D \leq R \leq D$, where D represents a diameter of said optical fiber.

25. A tumor treatment apparatus comprising:

a light source which emits a beam of light including ultraviolet radiation, visible radiation and infrared radiation;

an infrared radiation filter that filters infrared radiation;

a visible radiation filter that filters visible radiation, said visible radiation filter filtering only a portion of the visible radiation emitted by said light source;

a light transmitting system that transmits a beam of light consisting of ultraviolet radiation and filtered visible radiation, transmitted through said infrared radiation filter and said visible radiation filter, so that said beam of light consisting of ultraviolet radiation and filtered visible radiation is incident onto an affected area to be treated; and a positioning system that selectively positions said visible radiation filter in and out of the beam of light.

26. The tumor treatment apparatus according to claim 25, said infrared radiation filter comprises a reflecting mirror which reflects the light emitted from said light source towards an incident end of said light transmitting system.

27. The tumor treatment apparatus according to claim 26, said visible radiation filter is positioned between said reflecting mirror and said light transmitting system.

28. The tumor treatment apparatus according to claim 25, said selective positioning system comprising a turret, said visible radiation filter being mounted on said turret, rotation of said turret moving said visible radiation filter into and out of the beam of light.

29. The tumor treatment apparatus according to claim 28, said turret including an aperture diametrically opposite to said visible filter, or whereby filtered or unfiltered visible light can be emitted onto an affected area to be treated, in accordance with a position of said turret.

* * * * *

UNITED STATES PATENT AND TRADEMARK OFFICE
CERTIFICATE OF CORRECTION

PATENT NO. : 5,855,595
DATED : January 5, 1999
INVENTOR(S) : A. FUJISHIMA et al.

It is certified that error appears in the above-identified patent and that said Letters Patent is hereby corrected as shown below:

On the cover of the printed patent at item [56], References Cited FOREIGN PATENT DOCUMENTS, "2105195 3/1993 United Kingdom" should be —2105195 3/1983, United Kingdom—.

On the cover of the printed patent at item [56], References Cited FOREIGN PATENT DOCUMENTS, "9909850, 5/1994 WIPO" should be —94/09850, 5/1994 WIPO—.

Signed and Sealed this

Seventh Day of March, 2000

Attest:

Q. TODD DICKINSON

*Attesting Officer*        *Commissioner of Patents and Trademarks*